(12) United States Patent
Pandalis

(10) Patent No.: US 7,815,945 B2
(45) Date of Patent: Oct. 19, 2010

(54) MEDICAMENT FOR THE PREVENTION AND TREATMENT OF INFLUENZA

(76) Inventor: Georgios Pandalis, Fuchtenweg 3, Glandorf (DE) 49219

( * ) Notice: Subject to any disclaimer, the term of this patent is extended or adjusted under 35 U.S.C. 154(b) by 40 days.

(21) Appl. No.: 12/065,663

(22) PCT Filed: Sep. 13, 2006

(86) PCT No.: PCT/EP2006/008919

§ 371 (c)(1),
(2), (4) Date: Apr. 4, 2008

(87) PCT Pub. No.: WO2007/031297

PCT Pub. Date: Mar. 22, 2007

(65) Prior Publication Data

US 2008/0274214 A1    Nov. 6, 2008

Related U.S. Application Data

(60) Provisional application No. 60/785,603, filed on Mar. 24, 2006.

(30) Foreign Application Priority Data

Sep. 13, 2005    (EP) .................................. 05019934

(51) Int. Cl.
*A01N 65/00*    (2009.01)
(52) U.S. Cl. ..................................................... 424/725
(58) Field of Classification Search ........................ None
See application file for complete search history.

(56) References Cited

FOREIGN PATENT DOCUMENTS

DE            19821971    * 11/1999

OTHER PUBLICATIONS

International Search Report for PCT/EP2006/008919 dated May 18, 2007 (3 pages).
Verykokidou et al., "Antibacteriophage Properties of Some Greek Plant Extracts," International Journal of Pharmacognosy, vol. 33, No. 4, 1995, pp. 339-343.
Dr. Pandalis Naturprodukte, "Cystus® Creme," Feb. 21, 2005, XP-002369376 (1 page).
Dr. Pandalis Naturprodukte, Cystus® Mastitabs®, Feb. 16, 2005, XP-002369377 (1 page).
Sokmen et al., "In vitro antioxidant activity of polyphenol extracts with antiviral properties from *Geranium sanguineun* L," Life Sciences, vol. 76, No. 25, May 6, 2005, pp. 2981-2993.
Serkedjieva et al., "In vitro anti-influenza virus activity of a plant preparation from *Geranium sanguineum* L," Antiviral Research, vol. 37, No. 2, Feb. 1998, pp. 121-130.
Arzte Zeitung, "Pflanzen-Extrakt bremst die Vermehrung von Grippeviren," Sep. 26, 2005, XP-002428861 (2 pages).
Urheimische Notizen, "Keine Chance fur Viren—Urheimische Philosophie gegen Influenza," Oct. 21, 2005, XP-002428878 (2 pages).
Seitz, "Mit Cistus-Polyphenolen gegen Grippepandemie?," Dec. 21, 2006, XP-002428879 (1 page).
Van Ooijen, Helga; "Fight Against Bird Flu—Action Instead Of Prevention," Bayerischer Rundfunk Report Munchen, Program of Oct. 24, 2005, in German with English translation attached (7 pages).
International Preliminary Report On Patentability issued in corresponding International Patent Application No. PCT/EP2006/008919 dated Mar. 18, 2008 (8 pages).
Merzouki et al., "Wild medicinal plants used by local Bouhmed population (Morocco)," Fitoterapia, vol. LXVIII, No. 5, 1997, pp. 444-460 (17 pages).

* cited by examiner

*Primary Examiner*—Michael V Meller
(74) *Attorney, Agent, or Firm*—Kilyk & Bowersox, P.L.L.C.

(57) ABSTRACT

The invention relates to the use of an extract from plants of the genus *Cistus* for the preparation of a medicament for the prevention and treatment of influenza, in particular of the avian flu and viral strains derived from the avian flu in the course of an impending pandemic.

11 Claims, 16 Drawing Sheets

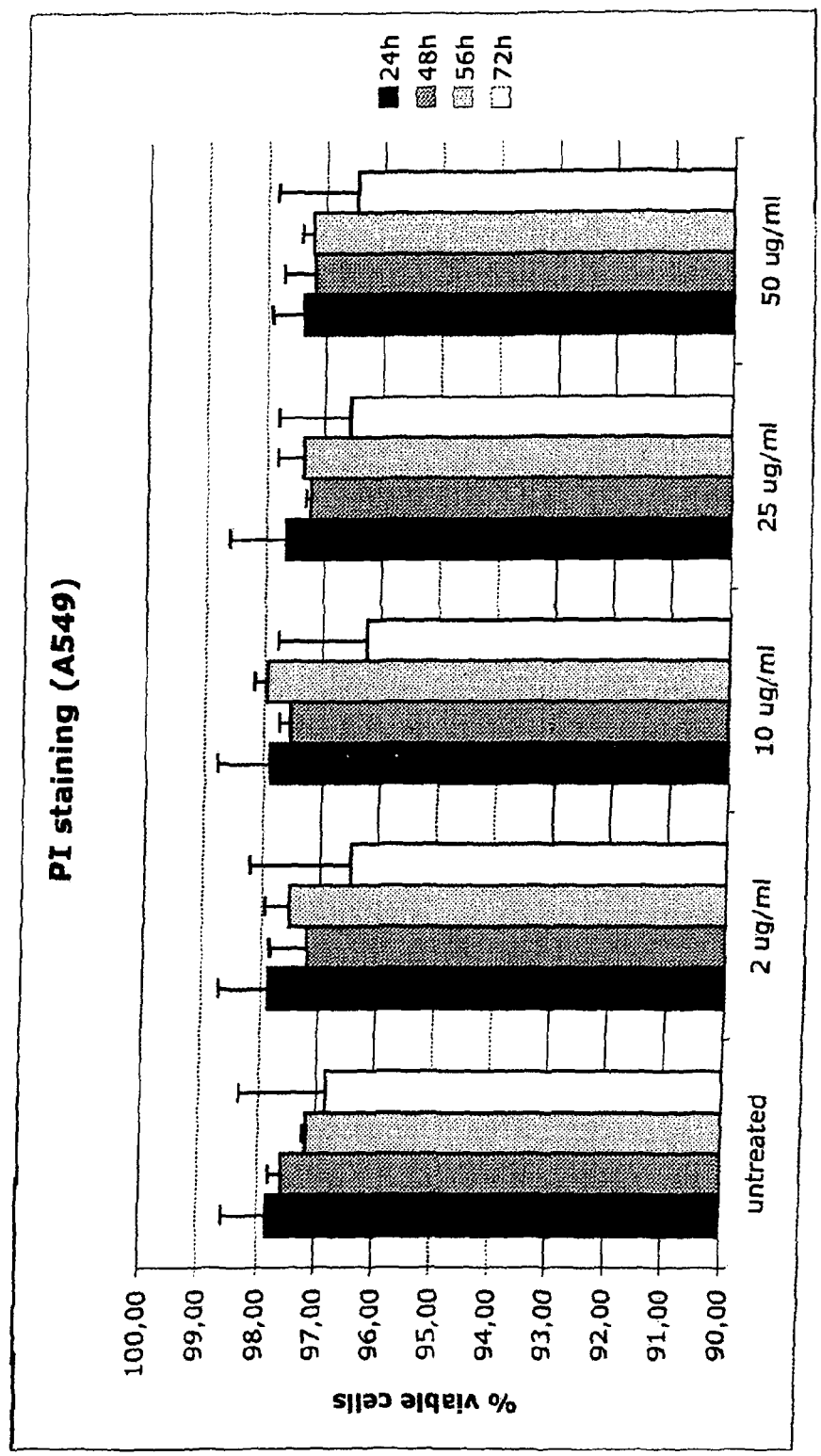
Figure 1. Viability test (PI Staining)

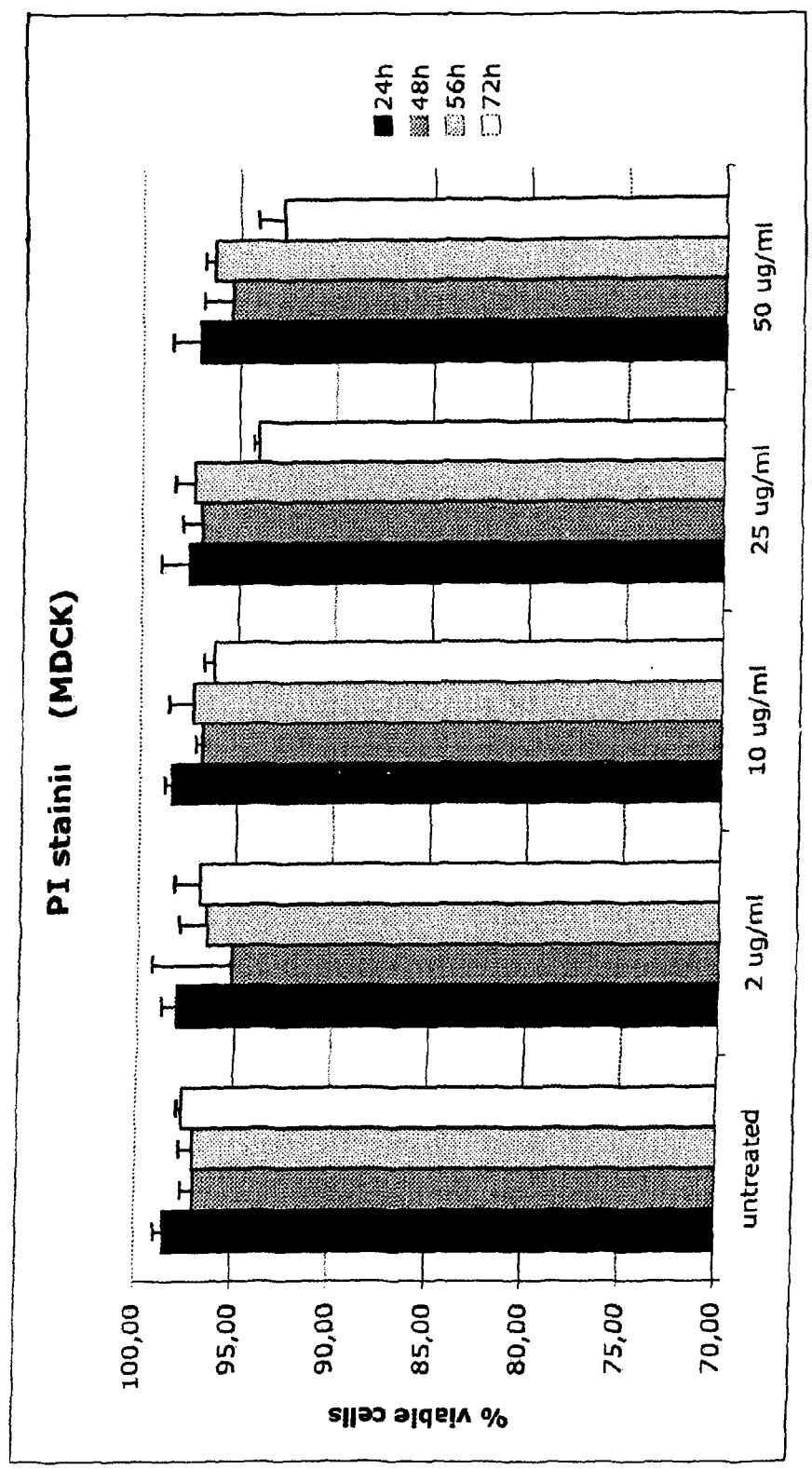
Figure 2. Viability test (PI staining)

Figure 3. Apoptosis test (PARP Blot)
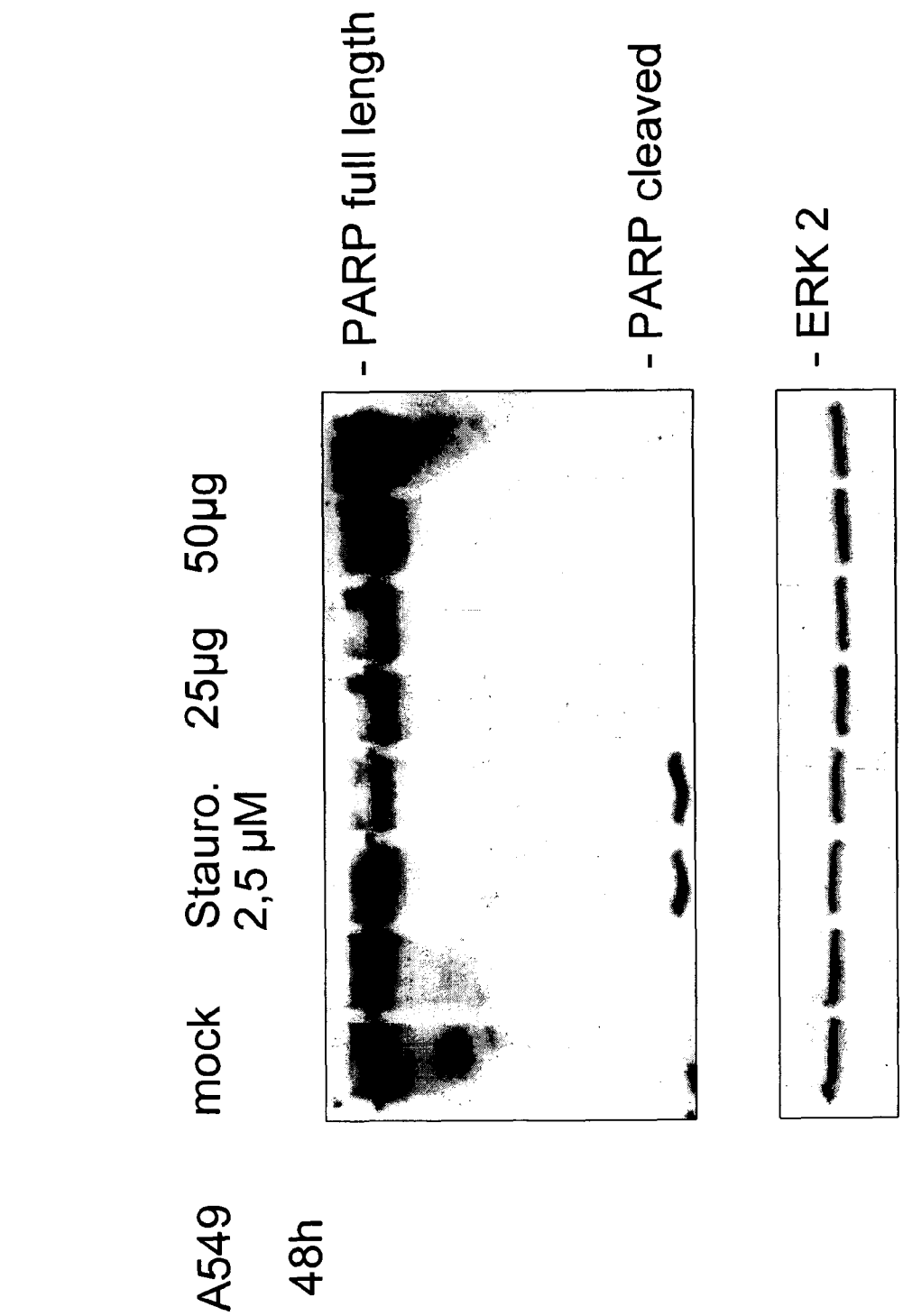

Figure 4. Virus Isolate FPV, Cell Line A549 h

Figure 4. Virus Isolate FPV, Cell Line A549

4h

Figure 4. Virus Isolate FPV, Cell Line A549

8h

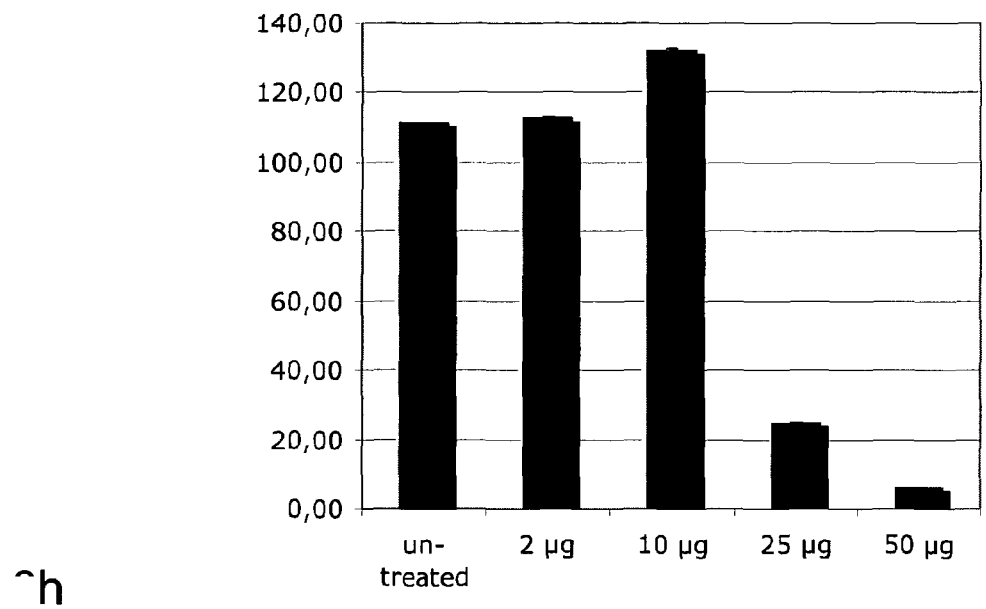
Figure 5. Virus Isolate FPV, Cell line MDCK.

Figure 5. Virus Isolate FPV, Cell line MDCK.
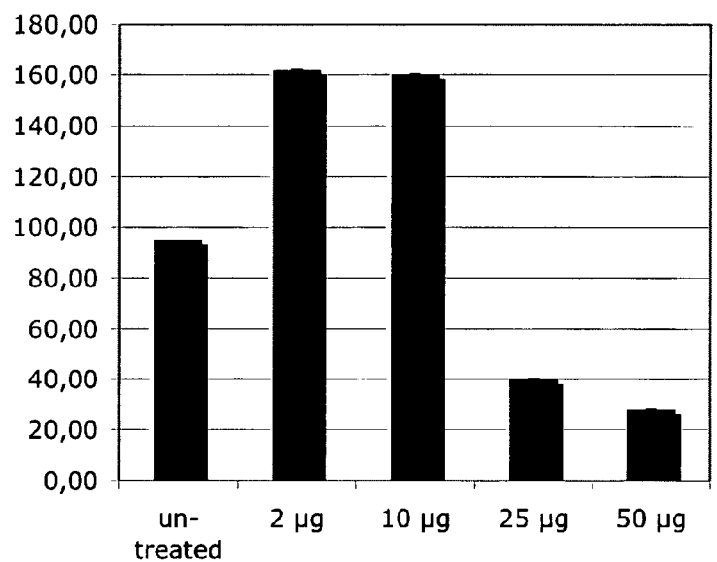
4h
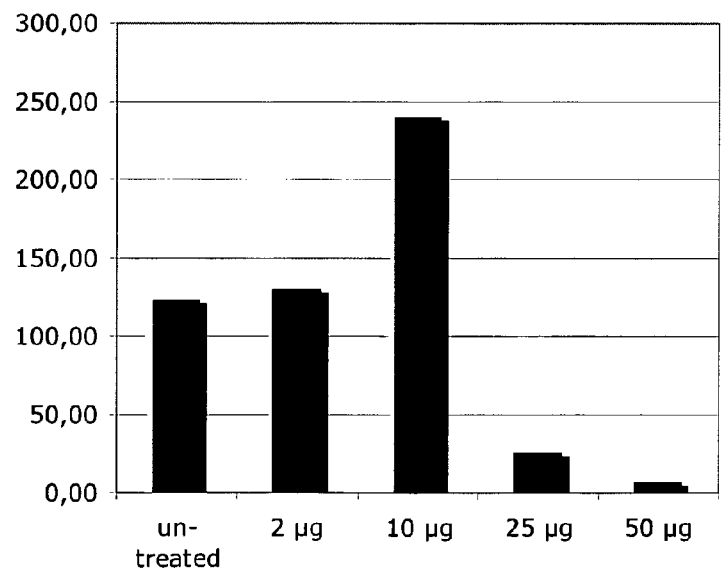

Figure 5. Virus Isolate FPV, Cell line MDCK.
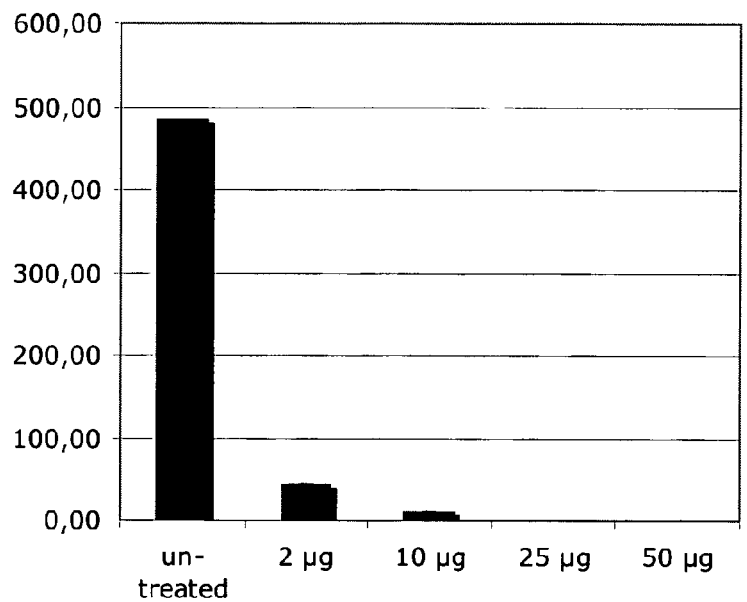
6h
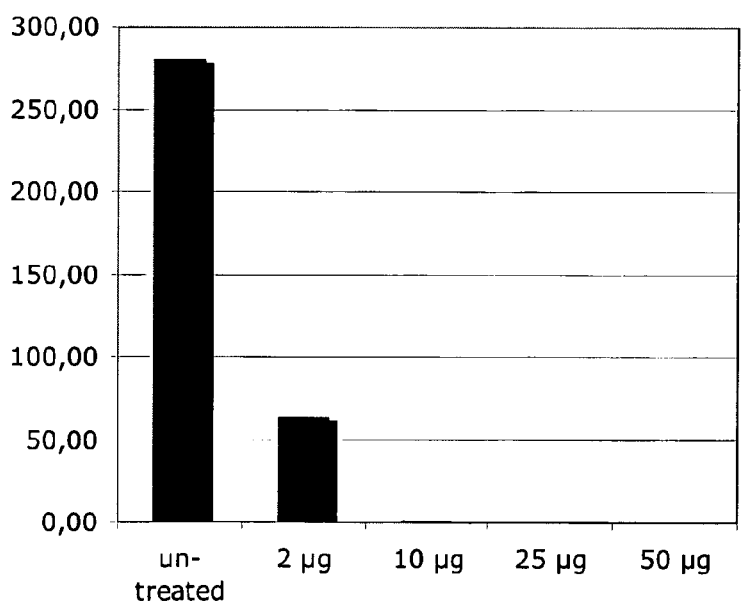

Figure 6. Virus Isolate PR8, Cell line MDCK.
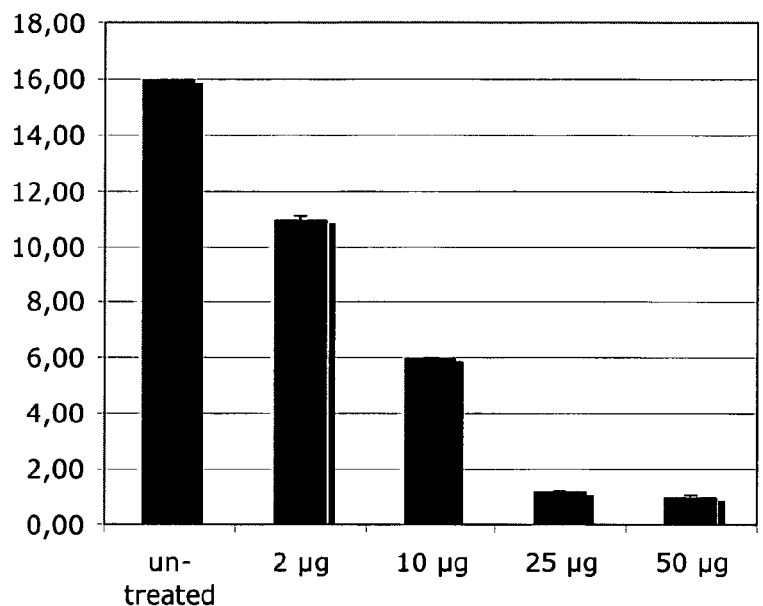
h
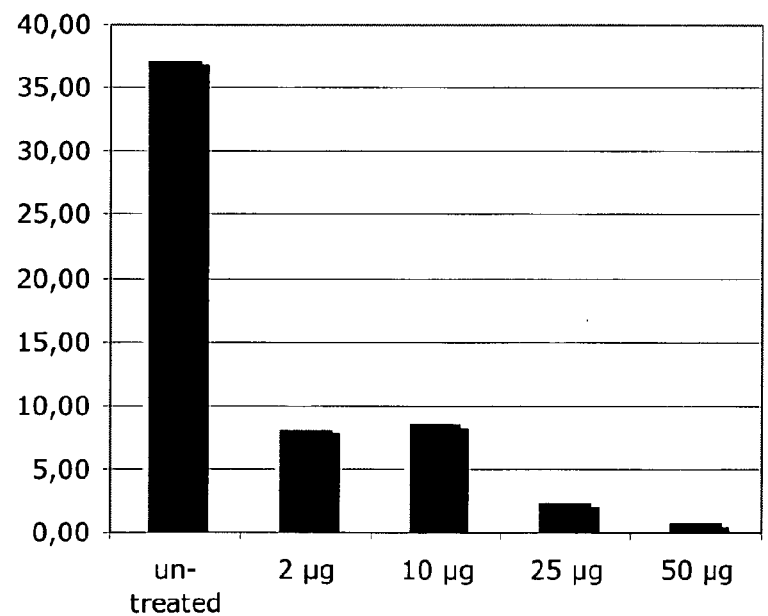

Figure 6. Virus Isolate PR8, Cell line MDCK.
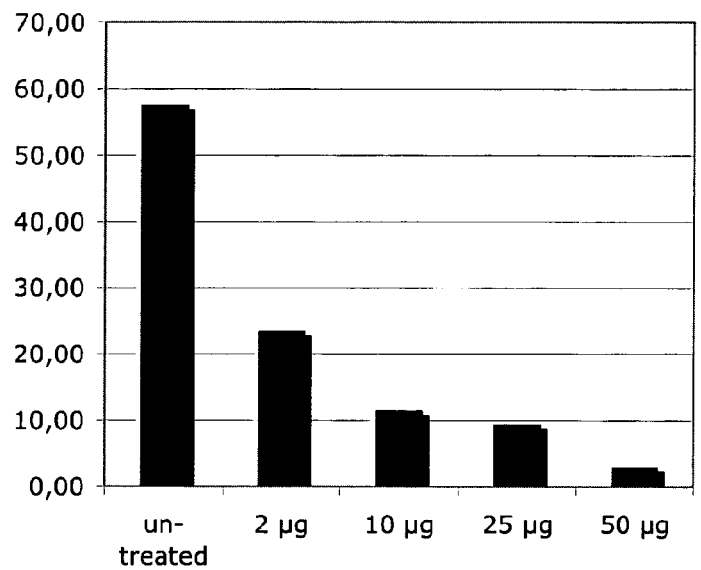
4h
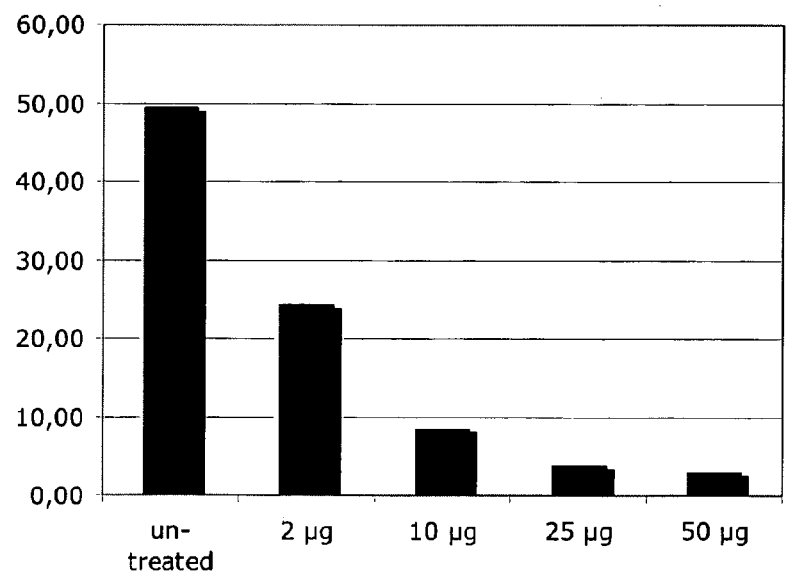

Figure 6. Virus Isolate PR8, Cell line MDCK.
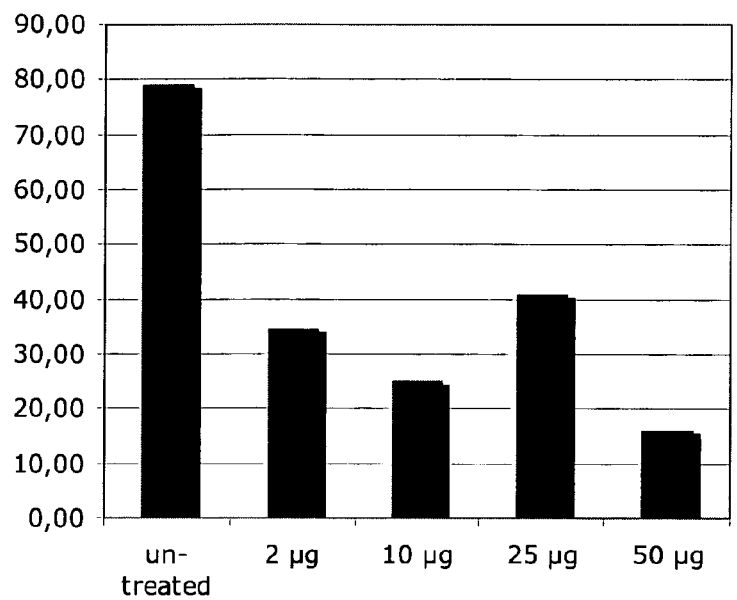
6h
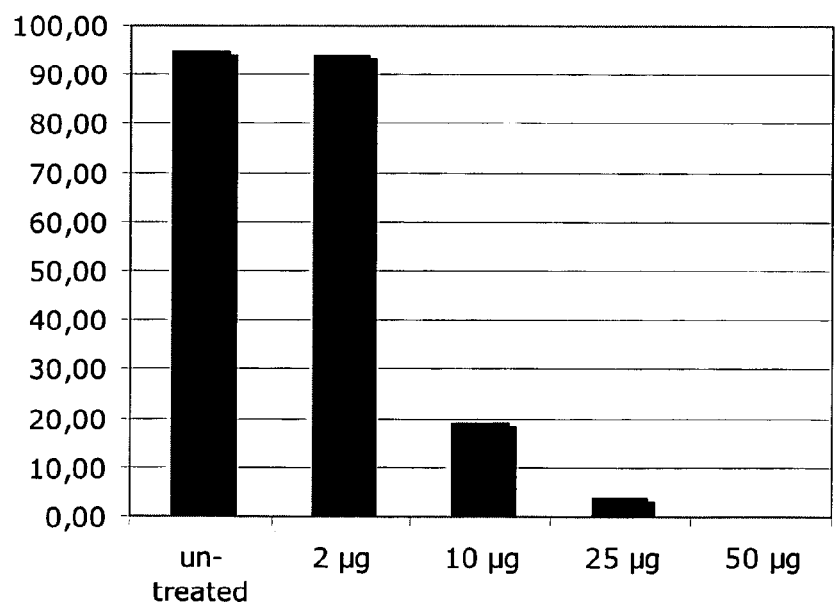

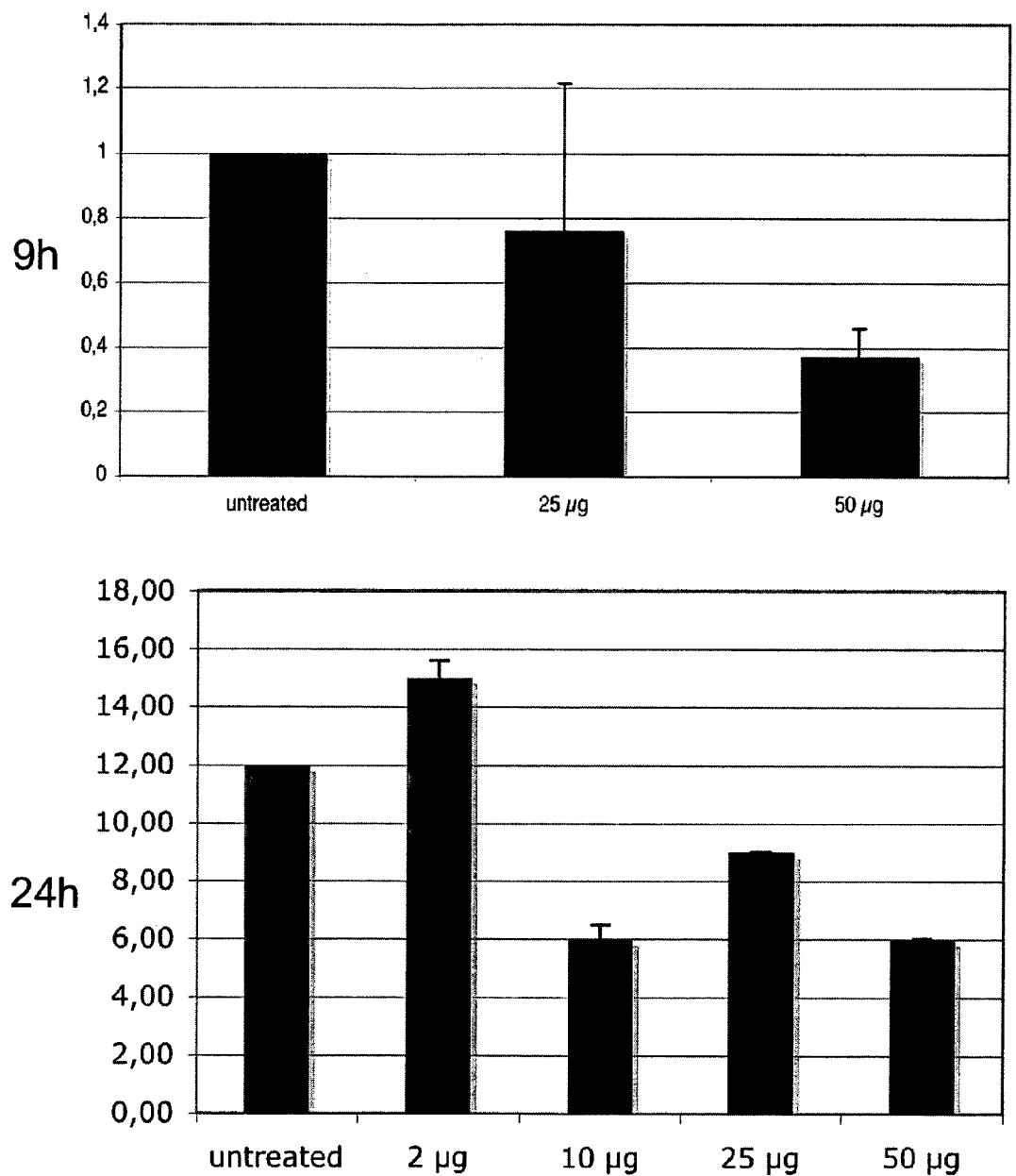
Figure 7. Virus Isolate PR8, Cell line A549.

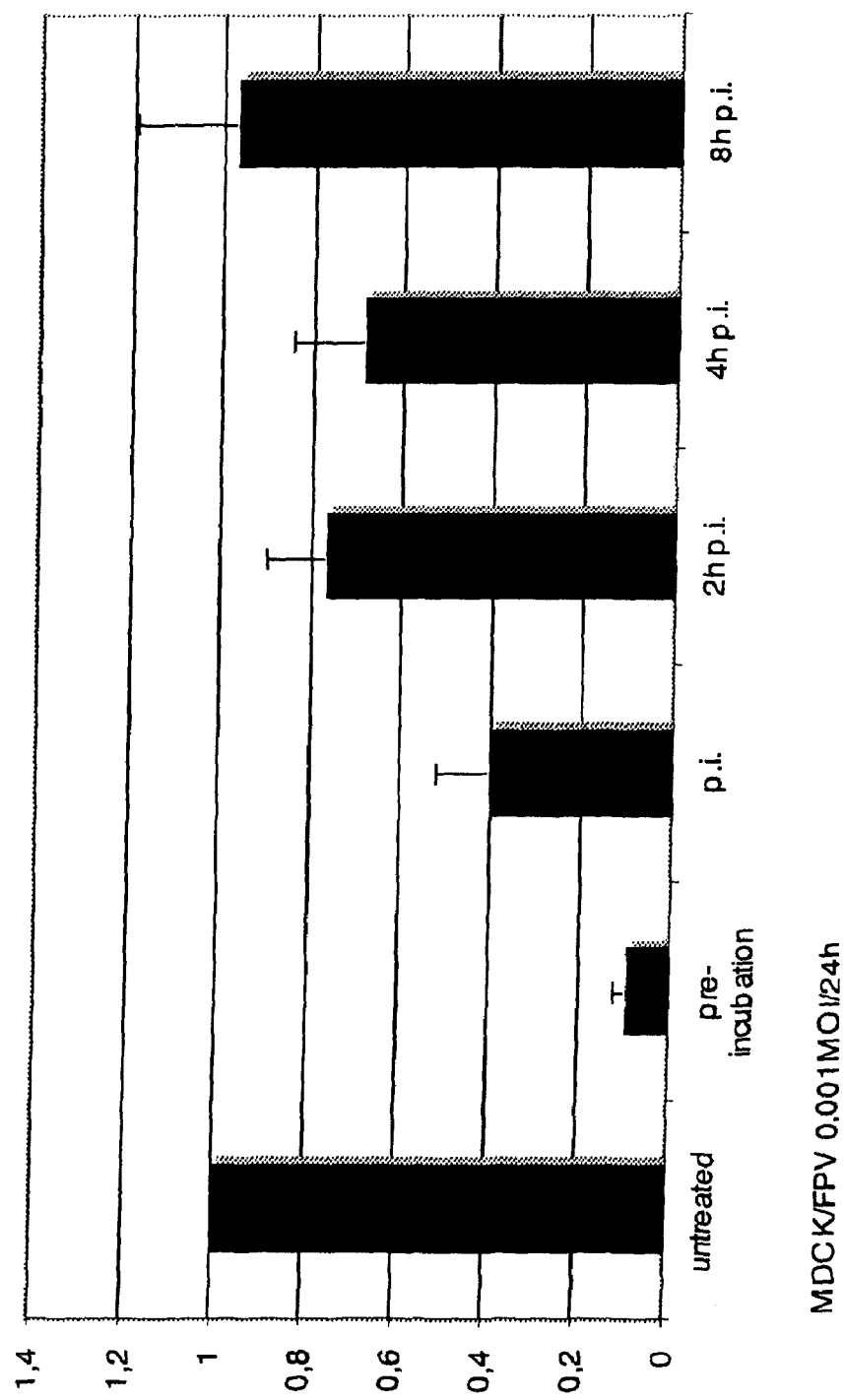
Figure 8. Virus Isolate FPV, Cell line MDCK.

Figure 9. Virus Isolate FPV, Cell Line MDCK.
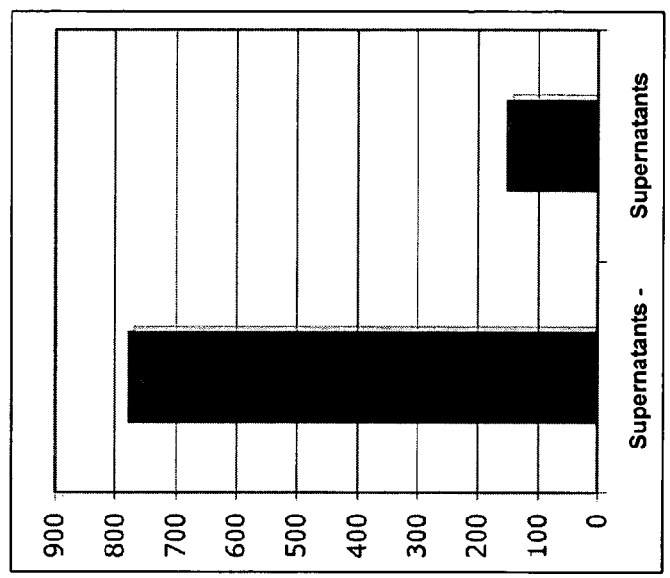
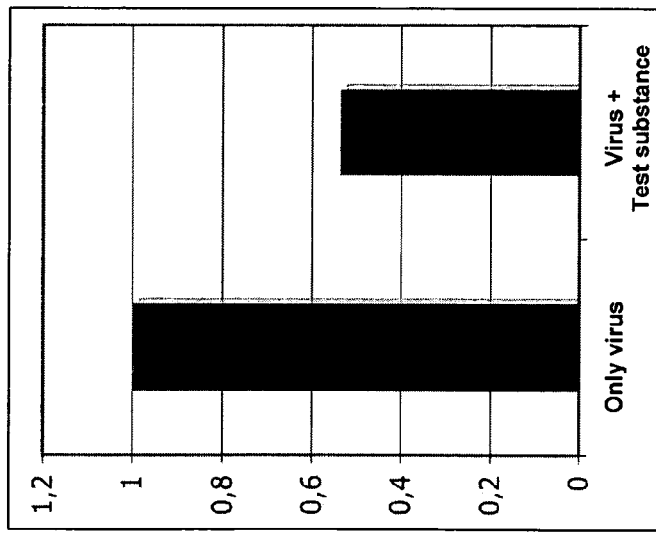

Figure 10.
Propagation ability of highly pathogenic H5N1 viruses

MEDICAMENT FOR THE PREVENTION AND TREATMENT OF INFLUENZA

This application is a National Stage Application of PCT/EP2006/008919, filed Sep. 13, 2006, which claims priority from European Patent Application No. 05019934.8, filed Sep. 13, 2005, and U.S. Provisional Patent Application No. 60/785,603, filed Mar. 24, 2006.

The present invention relates to the use of an extract for preparation of a medicament for the prevention and/or treatment of influenza.

Influenza, also known as flu, is a contagious viral disease which spreads around the world in seasonal epidemics. One distinguishes three virus types, A, B and C, B and C are restricted to humans, while type A extends to mammals and birds.

The World Health Organization, WHO, warns of a global influenza pandemic in the upcoming years. Epidemics and pandemics are mostly caused by influenza viruses of type A. Major genetic changes of the genetic material of influenza viruses have caused three pandemics in the 20$^{th}$ century, the infective agents of which were all of type A.

At present, the avian flu, also a type A virus, represents a particular danger of a pandemic. It has occurred increasingly in recent years, particularly in Southeast Asia. Its spread is aided by wild birds, which serve as resistant carriers of the disease. Experts fear that the avian flu virus could cross with an infective agent of the human flu. In principle, this is possible when pigs or humans are simultaneously infected with the avian flu and an infective agent of the human flu. This could lead to a virus which is highly contagious and deadly for humans, which could result in a global pandemic. Up until now, transmission of the avian flu to humans has only taken place locally. Transmission of the avian flu between humans was, however, not observed.

Vaccination represents the most important means of preventing of a viral sickness. However, in the context of prevention, vaccination depends on the preparation of a vaccine against a certain virus. This requires that the virus must already exist. This, and the long time needed for the development of a vaccine (approximately 4 months), lead to a substantial restriction in its use in a global pandemic. In such a case, the use of vaccines is only ensured by the prior and accompanying use of antiviral agents (*WHO Guidelines on the Use of Vaccines and Antivirals during Influenza Pandemics*; World Health Organization 2004).

Antiviral agents which are efficacious in treating influenza include amantadine, rimantadine, zanamivir, and oseltamivir und ribavirin. All listed medicaments have side effects which in some cases can be severe. For example, oseltamivir, which is sold under the name Tamiflu®, shows the frequent side effects of nausea, vomiting and stomach pain. Its use is indicated only after 13 years of age, as in some cases severe side effects such as ear infections, pneumonias, infections of the nasal sinuses, bronchitis, swelling of the lymph nodes, and conjunctivitis (Red List, Catalogue of Medication for Germany, 2004) were observed in youths under the age limit.

Antiviral medicaments are efficacious in the prophylaxis of a viral sickness as well as in its treatment. The direct medical cure of a viral sickness has not been successful thus far.

Further, an elderberry extract is known for its effect of shortening the duration of influenza under certain circumstances, without, however, demonstrating any appreciable preventative effect (Zakay-Rones, Z.; Varsano, N.; Zlotnik, M.; Manor, O.; Regev, L.; Schlesinger, M.; Mumcuoglu, M. *J. Altern. Complement. Med.* 1995, 1 (4), 361-9).

A germicidal effect is also known in extracts from plants of the genus *Cistus*. The *Cistus* species *incanus* and its subspecies *tauricus*, which are both prevalent in the Mediterranean region, have already been used in the traditional medicine of this region. *Cistus incanus* is used in livestock husbandry as a natural remedy as well as generally to increase the health condition of the animals (Pieroni, A.; Howard, P.; Volpato, G.; Santoro, R. F. *Vet. Res. Commun.* 2004, 28 (1), 55-80). In northern parts of Greece, *Cistus incanus* ssp. *tauricus* was traditionally used for the treatment of skin diseases (Petereit F., Kolodziej H., Nahrstedt A. *Phytochemistry* 1991, 30 (3), 981-985).

*Cistus* species contain, among other things, flavanoids and proanthocyanidines (Petereit F., Kolodziej H., Nahrstedt A. *Phytochemistry* 1991, 30 (3), 981-985), which can serve as antioxidants in the body (Attaguile, G.; Russo, A.; Campisi, A.; Savoca, F.; Acquaviva, R.; Ragusa, N.; Vanella, A. *Cell Biol Toxicol.* 2000, 16 (2), 83-90). Extracts of the leaves of *Cistus incanus* have antibacterial and antifungal activity (Bouamama, H. et al. *Therapie* 1999, 54 (6), 731-3).

As a preventative measure for the case of an impending pandemic which could be caused by the avian flu, the countries of the world community are counting on antiviral medicaments. For example, the medicament oseltamivir mentioned above (Tamiflu®; Hoffman La Roche) was ordered in significant amounts by some countries as a reserve for the case of a pandemic, although it is feared that the medicament could be quickly exhausted in an emergency. In addition, the immense demand has led to production bottlenecks.

In addition, the use of (known) antiviral agents is increasingly jeopardized by the fact that these are used as broad-spectrum medicaments in animal husbandry. Regardless of international bans, such practices have led for example in China to a resistance of some strains of the avian flu to these agents. In addition to this are the frequent side effects of these agents which in some cases can be severe. Further, in some cases these medicaments are only indicated for certain age groups, such as for example oseltamivir (Tamiflu®), which can only be used after 13 years of age.

BRIEF DESCRIPTION OF DRAWINGS

FIG. 1 and FIG. 2 are bar graphs showing viability testing (PI staining).

FIG. 3 is a Western blot analysis for the determination of caspase activity.

FIGS. 4-7 are a series of bar graphs for two independent experiments with multiple titer determination in comparison to titers from untreated infection samples.

FIG. 8 is a bar graph showing results from investigations of antiviral activity following preincubation of the viruses with extract.

FIG. 9A and FIG. 9B are bar graphs showing results from infection experiments with untreated viruses and pre-treated viruses.

FIG. 10A and FIG. 10B are bar graphs showing results for propagation ability of highly pathogenic H5N1 viruses.

The object of the present invention is therefore to provide an antiviral medicament for the prophylaxis and/or treatment of influenza, which can be economically prepared and which does not trigger any side effects in its administration.

This object is achieved by the use of an extract from plants of the genus *Cistus* for the preparation of a medicament for the prophylaxis and/or treatment of influenza.

The extract is isolated from a plant of the genus *Cistus*. 20 types of the genus *Cistus* are known:

*C. albidus* L.

*C. chinamadensis* Banares & P. Romero

*C. clusii* Dunal

*C. crispus* L.

*C. heterophyllus* Desf.

*C. incanus* (also known as *C. creticus*)

*C. inflatus* Pourr. Ex Demoly (also known as *C. hirsutus* Lam. or *C. psilosepalus* Sweet)

*C. ladanifer* L.

*C. laurifolius* L.

*C. libanotis* L.

*C. monspeliensis* L.

*C. munbyi* Pomel

*C. ochreatus* Chr. Sm. ex Buch

*C. osbeckilfolius* Webb ex Christ.

*C. parviflorus* Lam.

*C. populifolius* L.

*C. pouzolzii* Delile

*C. salviifolius* L.

*C. sintenisii* Litard. (also known as *C. albanicus* E. F. Warburg ex Heywood)

*C. symphytifolius* Lam.

The extract is preferably isolated from the species *C. incanus*. *C. incanus* includes two subspecies, *C. incanus* ssp. *tauricus* as well as *C. incanus* ssp. *undulatus*. Of these, the subspecies *C. incanus* ssp. *tauricus* is especially preferably used for extraction.

The extract is isolated from the aerial parts of the plants. Preferably, the aerial shoots of the plants which have regrown in the same year are used. The plant parts are subjected to an extraction directly following harvest, i.e. in raw condition. Alternatively, the plant parts are dried prior to the extraction. Subsequently, the leaves of the plant are minced in a suitable manner, for example by rubbing them or cutting them.

The extraction is carried out with a suitable solvent. Suitable solvents are water, alcohols such as methanol, ethanol or isopropanol, or chlorinated solvents such as dichloromethane, as well as acetone, acetyl acetone, ammonia, or glacial acetic acid. Mixtures of the named solvents may also be used. Preferably, a mixture of water with methanol or ethanol is used.

The extraction is typically performed at room temperature. However, it is also possible to perform the extraction at elevated temperatures of 25° C. up to, if necessary, the boiling point of the solvent used. An extraction at room temperature is preferred.

Fats such as lard, waxes such as beeswax, or oils such as olive oil and almond oil may further be used for the extraction. Almond oil is preferably used.

In order to achieve as high a yield as possible, the plant material may be extracted multiple times. Here, different solvents may be used in the different extraction steps, or an extraction with a solvent can be followed by an extraction with a fat, wax or oil, and vice-versa.

A liquid or semisolid crude product is obtained by the extraction, which may be used in this form for the preparation of a medicament for the prophylaxis and/or treatment of influenza.

The crude product may also be concentrated and/or dried and/or worked up further prior to the processing to a medicament. For example, the workup may include purification steps known to one of ordinary skill in the art, such as centrifugation, filtration, and decanting in order to remove suspended materials from the extract.

The present invention thus further relates to a dry extract. For the preparation of the dry extract, the solvent can be removed from the liquid crude extract, the concentrated extract, or the purified extract, for example by spray drying, freeze drying or vacuum drying.

The described extract is used for the prophylaxis and/or treatment of influenza.

Influenza infective agents are viruses of the type A, B and C. Seasonally occurring influenza in humans is caused by the influenza type A virus with the subtypes H1, H2, and H3, as well as by the influenza type B virus. The avian flu is primarily caused by the subtypes H5, H7, and H9.

The described extract is particularly suited for the prophylaxis and/or treatment of the avian flu. In particular, the extract can be used for the prophylaxis and/or treatment of avian flu caused by the subtype H7.

The extract can be used in any galenic application form known to one of ordinary skill in the art, for example as tablets, film tablets, capsules, powder, granulates, dragees, ointments, creams, gels, solutions, or sprays. The extract can also be used in the form of a powder for admixing into food, in particular into animal food.

Here, the extract can be processed with the common galenic adjuvants, such as tablet binders, fillers, preservatives, tablet degradation agents, flow regulators, softeners, wetting agents, dispersion agents, emulsifiers, solvents, retarding agents, antioxidants, consistency-conferring agents, agents for improving penetration and/or propellants.

The extract can also be mixed with other plant extracts, in particular with plant extracts with similar or synergetic effect.

Depending on the type of application, the concentration of the extract will vary in the form of use. Normally, the amount of the extract is between 1 to 1,000 mg per dosing unit in solid application forms. Preferably, the amount of extract is between 5 to 500 mg per unit. In fluid application forms, the extract may be present in a concentration of 1 µg/ml to 100 mg/ml, preferably of 25 µg/ml to 50 mg/ml. In semisolid application forms, the content of extract is 1 to 90 wt %, preferably 5 to 75 wt %.

The extract is preferably administered in the form of a tablet, wherein the extract is present as a dry extract.

It is further preferred to administer the extract in the form of ointments or creams for topical application. Here, an extract is used in which the active agents have been withdrawn from the plant by extraction with a fat, wax, or oil. It is further preferred that the dry extract is mixed with a fat, wax, or oil, or is dissolved in these.

It is further preferred that the extract is an aerosol. The aerosol can be used for the disinfection of objects and premises with which influenza-causing agents have come into contact or could potentially come into contact, in particular of animal husbandry facilities as well as means of transportation of any type in which humans, animals and/or foods are transported. For example, an airplane can be sprayed with the aerosol according to the invention prior to take-off to prevent a spreading of the avian flu and thus to minimize the danger of infection for the humans. The aerosol according to the invention can also be sprayed in the presence of humans, e.g. in waiting rooms, since it does not cause any toxic effects in humans.

The following example illustrates the present invention.

The extract was tested in respect of its cell toxicity and cell viability as well as is antiviral activity against influenza viruses. For this purpose, the extract was dissolved in PBS (sterile) by heating (1 h/100° C.) (stock solution 1 mg/ml). The dosages for the in vitro studies were 2, 10, 25, and 50 µg/ml system.

Influenza A Virus A/Bratislava/79 (H7N7) (FPV) (avian) as well as the Influenza A Virus A/Puerto-Rico/8/34 (H1N1) (PR8) (human) served as virus isolates.

Madin-Darby canine kidney (MDCK) cells, dog kidney epithelial cell line A549 cells, and human lung epithelial cell lines served as host cell lines.

The following test methods were used for the determination of the characteristics of the extract.

Microscopic Investigations:

In the microscopic investigations, A549 lung epithelial cells and MDCK dog kidney epithelial cells were treated for different time points (9 h, 24 h, 32 h, 48 h) with different concentrations of the extract (2, 10, 25, 50 µg/ml) and were subsequently investigated by light microscopy. The experiments were performed in duplicate with controls.

Viability Tests:

In the viability tests A549 lung epithelial cells and MDCK dog kidney epithelial cells were treated for different time points (24 h, 48 h, 56 h, 72 h) with different concentrations of the extract (2, 10, 25, 50 µg/ml) and were subsequently stained with propidium iodide to determine the ratio of dead and living cells by flow cytometry. The experiments were performed a total of four times.

Investigation of the Apoptotic Caspase Activation:

For the investigation of the apoptotic caspase activation, A549 cells were treated for 48 h with 25 and 50 µg/ml of the extract in addition to the agreed experiments. Following this, the cells were lysed, the cellular proteins were separated by gel electrophoresis, and were investigated by Western Blot with and anti-PARP antibody (poly(ADP-ribose)polymerase, caspase substrate) for the apoptotic cleavage of this protein by caspases. The apoptosis inductor staurosporine served as a positive control stimulus. The experiments were performed in two parallel batches.

Investigations of the Antiviral Activity:

For the investigations of the antiviral activity, A549 lung epithelial cells and MDCK dog kidney epithelial cells were pre-treated for 30 minutes with different concentrations of the extract (2, 10, 25, 50 µg/ml) for different time points and were subsequently infected with the influenza virus strains A/FPV/Bratislava/79 (H7N7) and A/PR8/34 (H1N1) in the presence of the extract. The medium supernatants were isolated at different time points following infection (8 h or 9 h, 24 h, 36 h or 48 h) and were investigated in plaque assays for newly formed influenza viruses.

Investigation of Effect Kinetics:

For the investigation of effect kinetics, MDCK cells were treated with 50 µg/ml of the extract for different time points (30 min preincubation, directly after infection, or 2 h, 4 h and 8 h after infection). The medium supernatants were investigated after 24 h for progeny viruses.

Investigation of the Antiviral Activity Following Preincubation of the Viruses with Extract:

For the investigation of the antiviral activity following preincubation of the viruses with extract, virus-containing infection solutions (FPV) were preincubated with 50 µg/ml of the extract for 2 h. An infection experiment in A549 cells was then performed with this infection solution in comparison to the untreated viruses, and after 24 h the newly formed viruses were detected in a virus titration. During this time, there was no longer any extract in the supernatant. The pre-treated viruses used for infection were further directly investigated in a plaque assay for their infectiousness in MDCK cells in comparison to untreated viruses.

Immunofluorescent Microscopic Investigations with Pre-Treated Viruses:

Virus-containing infection solutions (FPV) were preincubated with 50 μg/ml of the extract for 30 min or overnight. Untreated viruses as well as infection of pre-treated cells with viruses which had not been pre-treated served as a comparison. Then a comparative infection experiment with untreated viruses was performed with a high infection dose (MOI=200) and after 1 h, the infecting viruses or the newly formed protein was detected by immunofluorescence with the help of a specific antibody against a virus protein (nucleoprotein (NP)). The early detection time point and the high infection dose also allows the detection of infecting viruses or of virus aggregates.

The results from the investigations described above are shown graphically in FIGS. 1 to 9.

EXAMPLE

Preparation of an Extract from *Cistus incanus* ssp. *tauricus*

The regrown aerial shoots (leaves, petals, and stems) were used for extraction. The plant material is dried outdoors in the shade at room temperature until it has a residual water content of no more than 10%. Subsequently, the plant parts are cut to a size of <8 mm.

The cut plant parts are subjected to a percolation at 95° C. with the tenfold amount of purified water Ph.Eur. for 4 to 5 hours. The solution obtained is concentrated at a steam temperature of 75 to 80° C. to 18 to 19% of the original volume by means of a plate evaporator. The content of dry substance is approximately 45%.

The content of dry substance is increased to 50 to 51% by means of a stirring evaporator by heating the extract for 4 hours at 110 to 114° C. under reduced pressure (0.6 bar). Subsequently, the extract is boiled for 1 h at 100.3° C. to obtain a content dry substance of approximately 53%.

Finally, vacuum conveyor drying is performed at 16 mbar with decreasing temperature gradients (140° C., 120° C., 90° C., 20° C.). The content of dry substance is 92 to 93%. The extract is subsequently ground. The stock solution described above is then prepared from this extract.

Microscopic Investigations

In the microscope pictures, no significant changes with respect to cell number and cell morphology as compared to the untreated control samples could be determined for the investigation series with MDCK cells and A549 cells for any of the extract concentrations used or the time values investigated.

Viability Test Results of the viability test are shown in FIGS. 1 and 2, in which the number of the living cells from each of the respective samples are summarized comparatively as the average of the four determinations performed. The result was that no negative influence of the extract on the survival of MDCK or A549 cells could be determined in the entire observation period of 72 h.

Investigation of the Apoptotic Caspase Activation

Results from the investigation of the apoptotic caspase activation are shown in FIG. 3, which illustrates results of the western blot analysis for the determination of caspase activity. While the control stimulus staurosporine (stauro) leads to an efficient cleavage of the caspase substrate (poly(ADP-ribose)polymerase, band PARP cleaved), no such activity is detectable in either untreated (mock) or in extract-treated cells (25 µg/ml, 50 µg/ml). A control blot against the protein ERK2 served as a control for uniform protein loading. As a result it can be concluded that treatment with plant extract does not lead to caspase activation and apoptosis induction in the concentrations used and in the period observed.

Investigations of Antiviral Activity

In the investigations of the antiviral activity of the extract, FIG. 4-7 show exemplary results from each of two independent experiments with multiple titer determination. The virus titers are shown in comparison to the titers from untreated infection samples. In FPV-infected A549 cells, even lower concentrations lead to a significant reduction of the virus titers after 9 h and 24 h, which virus titers are reduced by more than two orders of magnitude at the highest concentration of active agent. Due to the high infection dose, the untreated samples are already in a plateau phase of virus growth after 48 h, so that the inhibitory effects can no longer be shown so clearly. Still, even here, a reduction of the virus titers is observed for the highest concentration of active agent. The greatest reduction of virus titers could also be found with the same virus isolate in MDCK cells in treating the samples with 25-50 µg/ml of the extract, wherein an inhibition by multiple orders of magnitude is also achieved. Surprisingly, a slight increase in virus titers is seen in some batches at lower concentrations of active agent. However, since this did not consistently occur in all samples and especially was not observable within the longest observation period of 36 h, it can be assumed that this is an experimental artefact.

A concentration-dependent inhibition of virus propagation in MDCK cells is also observed for the alternatively used human virus isolate PR8 at all investigated time values. In agreement with the previous experiments, here there was also a reduction in the virus titers at the highest active agent concentration of 50 µg/ml.

In summary, the statement can be made that, especially at extract concentrations of 25 µg/ml and 50 µg/ml, a strong inhibitory effect on the virus propagation of different influenza viruses is observed in the two host cell lines.

Investigation of the Effect Kinetics

Results from the investigations of antiviral activity following preincubation of the viruses with extract are shown graphically in FIG. 8. This investigation of the effect kinetics of comparative virus titers shows that a strongly inhibitory effect on virus propagation was only recognizable with pre-incubation of the cells with the extract. The extract did not show any further effect when it was added >2 h after infection.

Investigation of the Antiviral Activity Following Preincubation of the Viruses with Extract A comparative infection experiment with untreated viruses was performed with an infection solution which was preincubated with extract for 2 h, and the newly formed viruses were determined after 24 h in a virus titration (FIG. 9B). Further, the pre-treated viruses were directly investigated in a plaque assay for their infectiousness in comparison to untreated viruses (FIG. 9A). It turned out that the preincubation already had an effect in the direct determination of the infectiousness in the plaque assay. This became all the more evident when the extract-treated viruses versus untreated viruses were allowed an infection round for 24 h. Here, titer reductions of approximately one order of magnitude were recognizable.

In summary, one can say that the preincubation of the viruses with extract was already enough to contribute to a significant reduction of the infectiousness of the viruses.

Immunofluorescent Microscopic Investigations with Pre-Treated Viruses:

In the immunofluorescent microscopic investigations with pre-treated viruses, an elevated nucleoprotein (NP) concentration in the cell nucleus was already recognizable after 1 h, which shows that a major part of the NP-containing viral ribonucleoprotein complexes has migrated into the cell nucleus or that the production of new virus proteins has already begun. While this distribution differed only marginally in infected cells which were pre-treated with extract, a significant change was recognizable especially after preincubation of the infecting viruses overnight. Here, virus particles or aggregates were stained only at certain points and a concentration of the staining in the cell nucleus is hardly to be found. From this, one can conclude that the pre-treated viruses are only insufficiently able to infect the cells or be taken up into the cells.

The investigations of morphology, viability, and caspase activation of the cells treated with extract show that extract concentrations up to 50 µg/ml do not account for any significant toxic effect on the host cells A549 and MDCK used here, and induce neither enhanced necrotic nor apoptotic cell death. Further, no significant reduction in the number of cells could be recognized, so that cell growth is also not reduced by the effect of the extract. In summary, an evaluation of the results of antiviral activity of the extract taking into account experimental variances allows the statement that the extract demonstrates a significant and strong antiviral effect on the propagation of influenza viruses in cell culture in concentrations of 25-50 µg/ml.

The tested plant extract demonstrated an antiviral activity against influenza viruses in cell culture without being significantly toxic to the host cells. At the molecular level, the antiviral activity is assumed to be mediated in large part via a direct physical interaction of the components of the extract with the virus particle, although further additional effects of the extract on the cells cannot be ruled out.

In a further study, the virus inhibiting property of *Cistus* on highly pathogenic influenza viruses of the subtypes H5N1 (Asia flu) and H7N7 have been investigated. Virus isolate A/Thailand/1(KAN-1)/2005 (H5N1) (human) as well as the Influenza A Virus A/Bratislava/79 (H7N7) (FPV) (avian) served as virus isolates in the following study.

Inhibition of the Agglutination Ability of Highly Pathogenic H5N1 and H7N7 Viruses:

The *Cistus* extract was diluted to concentrations of ½, ¼, ⅛ ¹⁄₁₆ and ¹⁄₃₂ of the stock solution concentration. H5N1 and H7N7 virus isolutes were diluted to a final concentration of 1/64 of the original concentration. Each *Cistus* solution was mixed in a 96 well plate with 50 µl of the H5N1 solution (PFU: 4.5×10⁸) and the H7N7 solution (PFU: 5.7×10⁸), respectively, per well. The plate was incubated at 37° C. in a $CO_2$ incubator for one hour, then 50 µl of chicken blood diluted to 1/20 were added per well and the plate was again incubated for 30-45 minutes in a refrigerator. As a control, erythrocytes were either untreated or treated with H5N1 and H7N7, respectively, thereby omitting the *Cistus* extract.

As a result, it was found that the extract has the capability to effectively inhibit the crosslinking of erythrocytes in H5N1 and H7N7 virus isolates. Thus, extracts of *Cistus* are capable to significantly reduce the binding ability of hemagglutinin on cellular receptors in H5N1 and H7N7.

Inhibition of the Propagation Ability of Highly Pathogenic H5N1 Viruses:

A549 cells were disseminated and allowed to grow for 24 hours. Then, the cells were pre-incubated with *Cistus* extract for 30 minutes. Extract concentrations of 50 µg/ml, 75 µg/ml and 100 µg/ml were used. Likewise, the H5N1 virus was preincubated with the extract (50 µg/ml, 75 µg/ml and 100 µg/ml) for 30 minutes at room temperature. After preincubation the cells were infected with the influenza A virus subtype H5N1 (MOI: 0.001) for 30 minutes with occasional swiveling at 37° C. in a $CO_2$ incubator. Subsequently, the cells were washed with PBS to remove non-bonded viruses and incubated with *Cistus* extract (50 µg/ml, 75 µg/ml and 100 µg/ml) for 20 hours in the $CO_2$ incubator at 37° C. After 20 hours of incubation the supernatants were removed and the virus titer was measured via the plaque assay. Untreated infected samples were used as controls.

The results are shown in FIG. 10 wherein the untreated control sample has been set to represent 100%. Two different charges (A and B) of extract have been investigated.

As can be taken from FIG. 10, the extract significantly reduces the number of progeny viruses.

The invention claimed is:

1. A method for treating influenza comprising administering an extract from *cistus incanus* to a patient having influenza.

2. The method according to claim 1, wherein the extract is isolated from the aerial parts.

3. The method according to claim 1, wherein the extract is in liquid, dried, or semisolid form.

4. The method according to claim 1, wherein the extract is an aqueous extract or an alcoholic extract.

5. The method according to claim 1 for the treatment of the avian flu.

6. The method according to claim 1, wherein the extract is administered orally or topically.

7. The method according to claim 1, wherein the extract is sprayed.

8. The method of claim 2, wherein said extract is obtained by subjecting said aerial parts to percolation.

9. The method of claim 1, wherein said extract has a concentration of from 1 µg/ml to 100 mg/ml when the extract is in liquid form.

10. The method of claim 1, wherein said extract has a concentration of from 1 to 90 wt % when in semi-solid form.

11. The method of claim 1, wherein said extract has a concentration of from 5 to 75 wt % when present in semi-solid form.

* * * * *